US00RE48993E

(19) United States
(12) Reissued Patent
Stone et al.

(10) Patent Number: US RE48,993 E
(45) Date of Reissued Patent: Mar. 29, 2022

(54) FLUIDIC SYSTEM FOR REAGENT DELIVERY TO A FLOW CELL

(71) Applicant: Illumina, Inc., San Diego, CA (US)

(72) Inventors: Michael Stone, San Diego, CA (US); Drew Verkade, Carlsbad, CA (US)

(73) Assignee: ILLUMINA, INC., San Diego, CA (US)

(21) Appl. No.: 16/550,044

(22) Filed: Aug. 23, 2019

Related U.S. Patent Documents

Reissue of:
(64) Patent No.: 9,777,325
Issued: Oct. 3, 2017
Appl. No.: 15/204,717
Filed: Jul. 7, 2016

U.S. Applications:
(62) Division of application No. 14/453,868, filed on Aug. 7, 2014, now Pat. No. 9,410,977.
(Continued)

(51) Int. Cl.
*B01L 3/00* (2006.01)
*G01N 35/10* (2006.01)
(Continued)

(52) U.S. Cl.
CPC ..... *C12Q 1/6874* (2013.01); *B01L 3/502715* (2013.01); *B01L 3/502738* (2013.01);
(Continued)

(58) Field of Classification Search
CPC ..... C12Q 1/6874; B01L 3/502715; B01L 3/502738; B01L 3/527; B01L 2200/025; B01L 2200/026; B01L 2200/0621; B01L 2200/16; B01L 2300/0654; B01L 2300/0867; B01L 2300/0877;
(Continued)

(56) References Cited

U.S. PATENT DOCUMENTS 5,395,587 A 3/1995 Brigham-Burke et al.
5,641,658 A 6/1997 Adams et al.
(Continued)

FOREIGN PATENT DOCUMENTS

CA 2324354 9/1999
CN 101512018 8/2009
(Continued)

OTHER PUBLICATIONS

Bentley, et al., "Accurate whole human genome sequencing using reversible terminator chemistry," Nature, vol. 456, 2008, 53-59.

*Primary Examiner* — Elizabeth L McKane
(74) *Attorney, Agent, or Firm* — Illumina, Inc.

(57) ABSTRACT

A fluidic system that includes a reagent manifold comprising a plurality of channels configured for fluid communication between a reagent cartridge and an inlet of a flow cell; a plurality of reagent sippers extending downward from ports in the manifold, each of the reagent sippers configured to be placed into a reagent reservoir in a reagent cartridge so that liquid reagent can be drawn from the reagent reservoir into the sipper; at least one valve configured to mediate fluid communication between the reservoirs and the inlet of the flow cell. The reagent manifold can also include cache reservoirs for reagent re-use.

19 Claims, 11 Drawing Sheets

Related U.S. Application Data

(60) Provisional application No. 61/863,795, filed on Aug. 8, 2013.

(51) Int. Cl.

| | |
|---|---|
| ***C12Q 1/68*** | (2018.01) |
| ***B01L 3/02*** | (2006.01) |
| ***G01N 35/00*** | (2006.01) |
| ***G01N 21/64*** | (2006.01) |
| ***C12Q 1/6874*** | (2018.01) |

(52) U.S. Cl.

CPC ..... *B01L 3/527* (2013.01); *G01N 35/1097* (2013.01); *B01L 3/021* (2013.01); *B01L 3/0268* (2013.01); *B01L 3/0275* (2013.01); *B01L 2200/025* (2013.01); *B01L 2200/026* (2013.01); *B01L 2200/0621* (2013.01); *B01L 2200/16* (2013.01); *B01L 2300/0654* (2013.01); *B01L 2300/0867* (2013.01); *B01L 2300/0877* (2013.01); *B01L 2300/0883* (2013.01); *B01L 2300/0887* (2013.01); *B01L 2300/168* (2013.01); *B01L 2400/02* (2013.01); *B01L 2400/0622* (2013.01); *B01L 2400/086* (2013.01); *G01N 21/6428* (2013.01); *G01N 21/6456* (2013.01); *G01N 35/1002* (2013.01); *G01N 35/1016* (2013.01); *G01N 35/1065* (2013.01); *G01N 2035/00237* (2013.01); *Y10T 436/2575* (2015.01)

(58) Field of Classification Search

CPC ..... B01L 2300/0883; B01L 2300/0887; B01L 2300/168; B01L 2400/02; B01L 2400/0622; B01L 2400/086; G01N 35/1097; G01N 35/1002; G01N 35/1016; G01N 35/1065; G01N 21/6428; G01N 21/6456

See application file for complete search history.

(56) References Cited

U.S. PATENT DOCUMENTS

| | | | | |
|---|---|---|---|---|
| 5,792,431 | A * | 8/1998 | Moore | C07K 1/047 422/116 |
| 5,891,734 | A | 4/1999 | Gill et al. | |
| 6,182,719 | B1 | 2/2001 | Yahiro | |
| 6,238,910 | B1 | 5/2001 | Custance et al. | |
| 7,057,026 | B2 | 6/2006 | Barnes et al. | |
| 7,115,400 | B1 | 10/2006 | Adessi et al. | |
| 7,211,414 | B2 | 5/2007 | Hardin et al. | |
| 7,315,019 | B2 | 1/2008 | Turner et al. | |
| 7,329,492 | B2 | 2/2008 | Hardin et al. | |
| 7,405,281 | B2 | 7/2008 | Xu et al. | |
| 8,173,080 | B2 | 5/2012 | Lebl et al. | |
| 8,354,080 | B2 | 1/2013 | Tsao et al. | |
| 8,404,198 | B2 | 3/2013 | Amshey | |
| 8,597,594 | B2 | 12/2013 | Posner et al. | |
| 8,748,789 | B2 | 6/2014 | Triener et al. | |
| 2002/0055100 | A1 | 5/2002 | Kawashima et al. | |
| 2003/0072679 | A1 | 4/2003 | Johnson et al. | |
| 2003/0167822 | A1 | 9/2003 | Johnson | |
| 2003/0175163 | A1 | 9/2003 | Shvets et al. | |
| 2004/0002090 | A1 | 1/2004 | Mayer et al. | |
| 2004/0096853 | A1 | 5/2004 | Mayer | |
| 2005/0106707 | A1 * | 5/2005 | Neimark | B01J 19/0046 435/287.1 |
| 2005/0129584 | A1 | 6/2005 | Johnson et al. | |
| 2005/0221281 | A1 | 10/2005 | Ho | |
| 2006/0223169 | A1 | 10/2006 | Bedingham et al. | |
| 2007/0128624 | A1 | 6/2007 | Gormley et al. | |
| 2007/0212267 | A1 | 9/2007 | Organ | |
| 2008/0009420 | A1 | 1/2008 | Schroth et al. | |
| 2008/0047836 | A1 | 2/2008 | Strand et al. | |
| 2008/0056948 | A1 | 3/2008 | Dale | |
| 2008/0058512 | A1 | 3/2008 | Leproust | |
| 2008/0108082 | A1 | 5/2008 | Rank et al. | |
| 2008/0249469 | A1 | 10/2008 | Selvaganapathy et al. | |
| 2009/0093625 | A1 * | 4/2009 | Chi | B01J 19/0046 536/25.4 |
| 2009/0155123 | A1 | 6/2009 | Williams et al. | |
| 2010/0009871 | A1 | 1/2010 | Reed et al. | |
| 2010/0300895 | A1 * | 12/2010 | Nobile | G01N 27/4145 205/775 |
| 2010/0323350 | A1 | 12/2010 | Gordon | |
| 2011/0008223 | A1 | 1/2011 | Tsao et al. | |
| 2011/0139752 | A1 | 6/2011 | Carter | |
| 2011/0287447 | A1 | 11/2011 | Noderhaug et al. | |
| 2012/0028364 | A1 | 2/2012 | Kraus et al. | |
| 2012/0178091 | A1 | 7/2012 | Glezer et al. | |
| 2012/0270305 | A1 | 10/2012 | Reed et al. | |
| 2013/0079232 | A1 | 3/2013 | Kain | |
| 2013/0130243 | A1 | 5/2013 | Livache et al. | |
| 2013/0260372 | A1 * | 10/2013 | Buermann | G01N 21/6428 435/6.1 |
| 2013/0316336 | A1 | 11/2013 | Matsui et al. | |
| 2014/0017687 | A1 * | 1/2014 | Wimberger-Friedl | C12Q 1/6869 435/6.11 |
| 2014/0345372 | A1 | 11/2014 | Gerhardt et al. | |

FOREIGN PATENT DOCUMENTS

| | | |
|---|---|---|
| CN | 101566489 | 10/2019 |
| EP | 1664335 | 6/2006 |
| JP | S56057690 | 5/1981 |
| JP | S5854558 | 4/1983 |
| JP | H09500208 | 1/1997 |
| JP | H11326341 | 11/1999 |
| JP | 2001523812 | 11/2001 |
| JP | 2002206994 | 7/2002 |
| JP | 2005534896 | 11/2005 |
| JP | 2010502217 | 1/2010 |
| JP | 2012506995 | 3/2012 |
| JP | 2013515260 | 5/2013 |
| WO | 1991/006678 | 5/1991 |
| WO | 1999/025476 | 5/1999 |
| WO | 2003/104771 | 12/2003 |
| WO | 2004/018497 | 3/2004 |
| WO | 2007/024778 | 3/2007 |
| WO | 2007/123744 | 11/2007 |
| WO | 2009/086556 | 7/2009 |
| WO | 2011/078777 | 6/2011 |

* cited by examiner

FLUIDIC SYSTEM FOR REAGENT DELIVERY TO A FLOW CELL

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

This application *is a reissue application of U.S. Pat. No. 9,777,325, which issued on Oct. 3, 2017 from U.S. patent application Ser. No. 15/204,717, filed Jul. 7, 2016, which* is a divisional of U.S. patent application Ser. No. 14/453,868, filed Aug. 7, 2014[, now pending,] *and issued as U.S. Pat. No. 9,410,977,* which claims the benefit of[,] U.S. Provisional Application No. 61/863,795, filed Aug. 8, 2013, each of which is incorporated herein by reference.

BACKGROUND

Embodiments of the present disclosure relate generally to apparatus and methods for fluidic manipulation and optical detection of samples, for example, in nucleic acid sequencing procedures.

Our genome provides a blue print for predicting many of our inherent predispositions such as our preferences, talents, susceptibility to disease and responsiveness to therapeutic drugs. An individual human genome contains a sequence of over 3 billion nucleotides. Differences in just a fraction of those nucleotides impart many of our unique characteristics. The research community is making impressive strides in unraveling the features that make up the blue print and with that a more complete understanding of how the information in each blue print relates to human health. However, our understanding is far from complete and this is hindering movement of the information from research labs to the clinic where the hope is that one day each of us will have a copy of our own personal genome so that we can sit down with our doctor to determine appropriate choices for a healthy lifestyle or a proper course of treatment.

The current bottleneck is a matter of throughput and scale. A fundamental component of unraveling the blue print for any given individual is to determine the exact sequence of the 3 billion nucleotides in their genome. Techniques are available to do this, but those techniques typically take many days and thousands upon thousands of dollars to perform. Furthermore, clinical relevance of any individual's genomic sequence is a matter of comparing unique features of their genomic sequence (i.e. their genotype) to reference genomes that are correlated with known characteristics (i.e. phenotypes). The issue of scale and throughput becomes evident when one considers that the reference genomes are created based on correlations of genotype to phenotype that arise from research studies that typically use thousands of individuals in order to be statistically valid. Thus, billions of nucleotides can eventually be sequenced for thousands of individuals to identify any clinically relevant genotype to phenotype correlation. Multiplied further by the number of diseases, drug responses, and other clinically relevant characteristics, the need for very inexpensive and rapid sequencing technologies becomes ever more apparent.

What is needed is a reduction in the cost of sequencing that drives large genetic correlation studies carried out by research scientists and that makes sequencing accessible in the clinical environment for the treatment of individual patients making life changing decisions. Embodiments of the invention set forth herein satisfy this need and provide other advantages as well.

BRIEF SUMMARY

The present disclosure provides a fluidic system that includes a reagent manifold comprising a plurality of channels configured for fluid communication between a reagent cartridge and an inlet of a flow cell; a plurality of reagent sippers extending downward from ports in the manifold, each of the reagent sippers configured to be placed into a reagent reservoir in a reagent cartridge so that liquid reagent can be drawn from the reagent reservoir into the sipper; at least one valve configured to mediate fluid communication between the reservoirs and the inlet of the flow cell.

This disclosure further provides a reagent cartridge that includes a plurality of reagent reservoirs configured to simultaneously engage a plurality of reagent sippers of a fluidic system along a z dimension such that liquid reagent can be drawn from the reagent reservoir into the sippers, the reagent reservoirs arranged in x and y dimensions into top, middle and bottom rows, wherein reagent reservoirs along top and bottom rows of the cartridge are deeper along the z dimension than reagent reservoirs in one or more middle rows; and at least two interface slots configured to engage with corresponding alignment pins of the fluidic system.

Also provided is a multi-layer diffusion bonded reagent manifold comprising at least 10, 15, or at least 20 ports, each port configured to pull reagent from a separate reagent reservoir via a sipper, wherein the ports are in fluid communication with one or more channels of a flow cell via fluidic channels in the manifold.

This disclosure further provides a method of reagent re-use that includes a) drawing a liquid reagent from a reagent reservoir into a cache reservoir, the cache reservoir in fluid communication with the reagent reservoir and at least one channel of a flow cell; b) transporting the reagent from the cache reservoir onto the at least one channel of the flow cell; c) transporting at least 30%, 40%, 50%, 60%, 70%, 80%, 90%, or 100% of the reagent on the flow cell channel to the cache reservoir such that the liquid reagent from the flow cell is not directed back to the reagent reservoir after contacting the flow cell; and d) repeating steps b) and c) to achieve re-use of the liquid reagent on the flow cell.

This disclosure further provides a sequencing method that includes the steps of (a) providing a fluidic system comprising (i) a flow cell comprising an optically transparent surface, (ii) a nucleic acid sample, (iii) a plurality of reagents for a sequencing reaction, and (iv) a fluidic system for delivering the reagents to the flow cell; (b) providing a detection apparatus comprising (i) a plurality of microfluorometers, wherein each of the microfluorometers comprises an objective configured for wide-field image detection in an image plane in x and y dimensions, and (ii) a sample stage; and (c) carrying out fluidic operations of a nucleic acid sequencing procedure in the cartridge and detection operations of the nucleic acid sequencing procedure in the detection apparatus, wherein (i) the reagents are delivered to the flow cell by the fluidic system, (ii) wide-field images of the nucleic acid features are detected by the plurality of microfluorometers, and (iii) at least some reagents are removed from the flow cell to a cache reservoir.

The details of one or more embodiments are set forth in the accompanying drawings and the description below.

Other features, objects, and advantages will be apparent from the description and drawings, and from the claims.

DETAILED DESCRIPTION

This disclosure provides fluidic systems and methods for providing reagents to a chamber such as a flow cell. A particularly useful application is detection of an immobilized biological sample. For example, the methods and systems set forth herein can be used in nucleic acid sequencing applications. A variety of nucleic acid sequencing techniques that utilize optically and non-optically detectable samples and/or reagents can be used. These techniques are particularly well suited to the methods and apparatus of the present disclosure and therefore highlight various advantages for particular embodiments of the invention. Some of those advantages are set forth below for purposes of illustration and, although nucleic acid sequencing applications are exemplified, the advantages can be extended to other applications as well.

The fluidic systems set forth herein are particularly useful with any of the detection apparatus configurations and sequencing methods set forth in U.S. patent application Ser. No. 13/766,413 filed on Feb. 13, 2013 and entitled "INTEGRATED OPTOELECTRONIC READ HEAD AND FLUIDIC CARTRIDGE USEFUL FOR NUCLEIC ACID SEQUENCING," the content of which is incorporated by reference in its entirety.

In particular embodiments, a sample that is to be detected can be provided to a detection chamber using a fluidic system as provided herein. Taking the more specific example of a nucleic acid sequencing application, the fluidic system can include a manifold assembly that can be placed into fluidic communication with one or more of reservoirs for holding sequencing reagents, reservoirs for holding sample preparation reagents, reservoirs for holding waste products generated during sequencing, and/or pumps, valves and other components capable of moving fluids through a flow cell.

In particular embodiments a fluidic system can be configured to allow re-use of one or more reagents. For example, the fluidic system can be configured to deliver a reagent to a flow cell, then remove the reagent from the flow cell, and then re-introduce the reagent to the flow cell. An advantage of re-using reagents is to reduce waste volume and reduce the cost of processes that utilize expensive reagents and/or reagents that are delivered at high concentrations (or in high amounts). Reagent re-use takes advantage of the understanding that depletion of reagent occurs only or primarily at the flowcell surface, and therefore a majority of the reagent goes unused and may be subject to re-use.

Figure 1A:
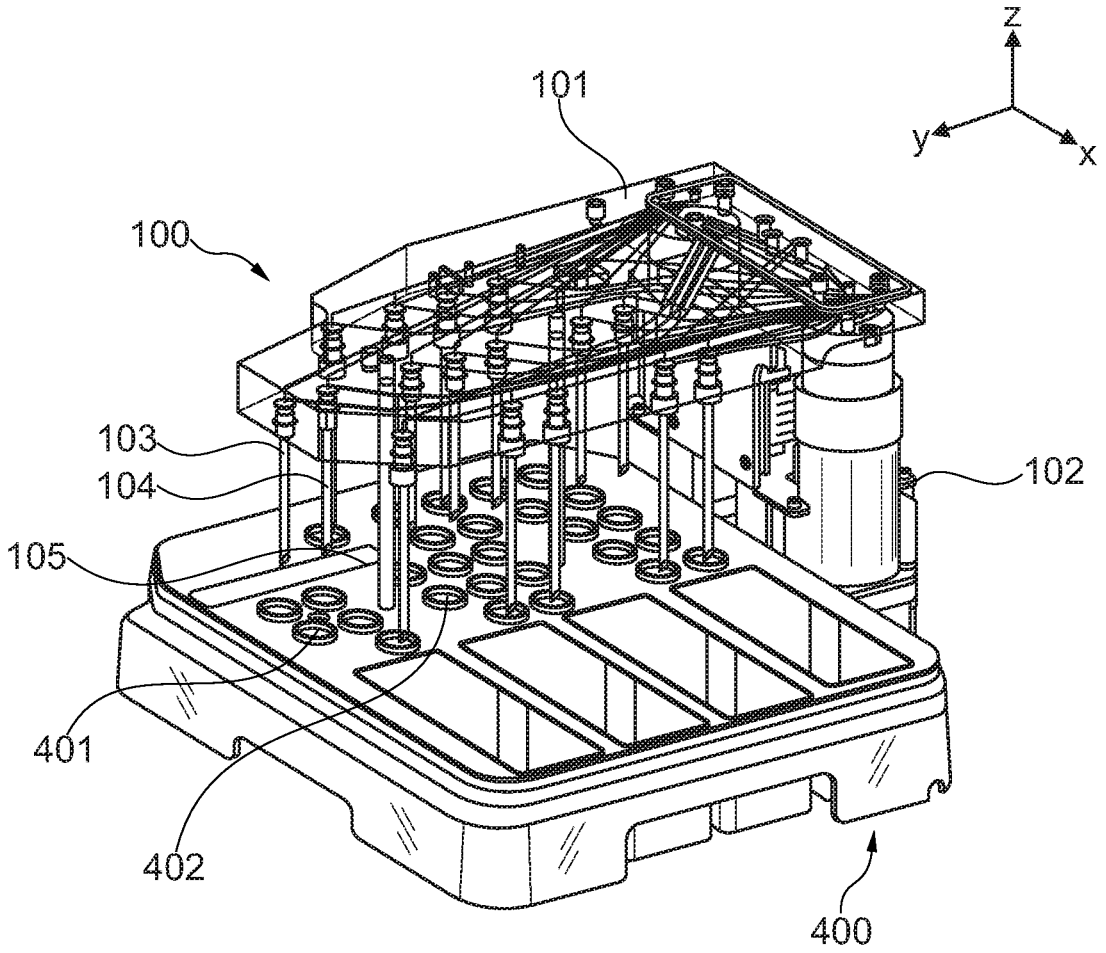
FIG. 1A shows a fluidic system with reagent sippers interacting with a reagent cartridge.

FIG. 1A shows an exemplary fluidic system 100 having reagent sippers 103 and 104 and valves 102 that exploits advantages of fluidic systems that are provided by several embodiments set forth herein. The fluidic system 100 includes a manifold assembly 101 that contains various fixed components including, for example, reagent sippers, valves, channels, reservoirs and the like. A reagent cartridge 400 is present having reagent reservoirs 401 and 402 configured to simultaneously engage a set of reagent sippers 103 and 104 along a dimension z such that liquid reagent can be drawn from the reagent reservoirs into the sippers.

Figure 1B:
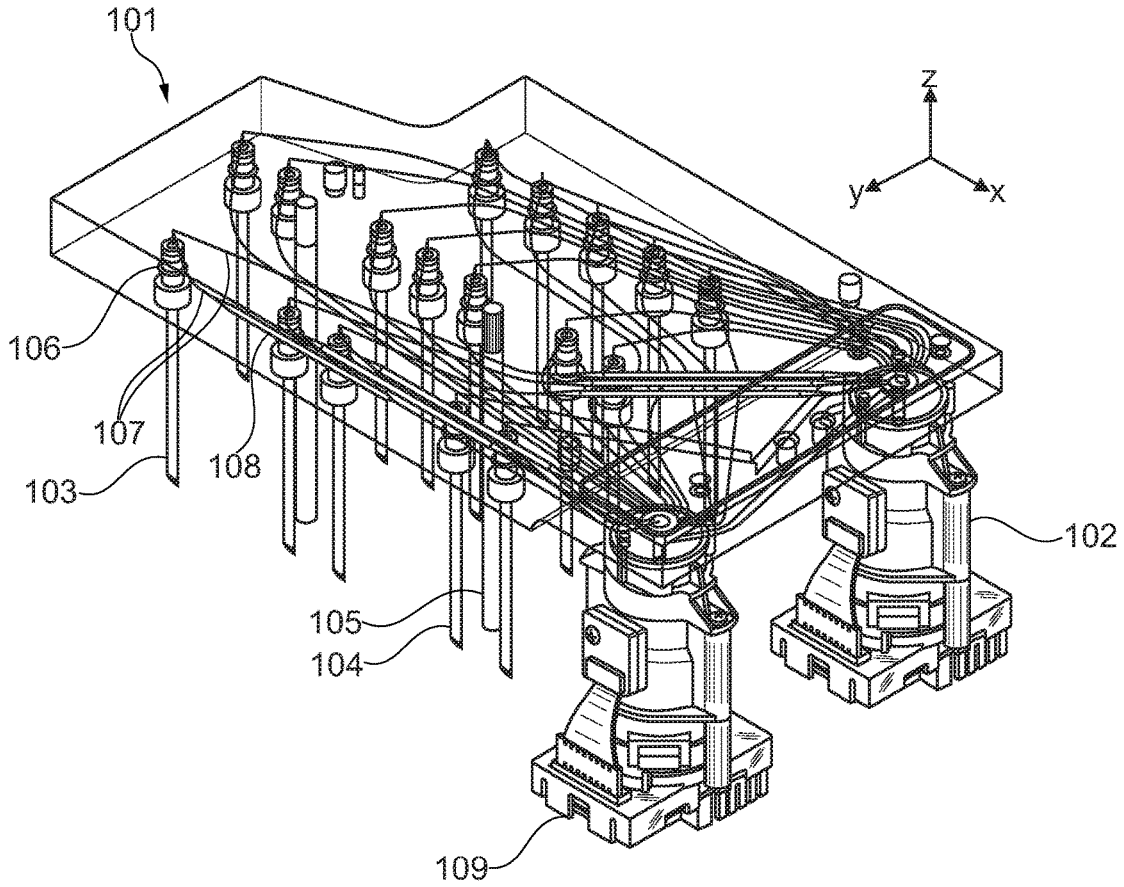
FIG. 1B shows an isometric view of a manifold assembly and displays an example of a layout of fluidic channels within the manifold.

Shown in FIG. 1B is an exemplary manifold assembly 101 that can be used to provide liquid reagents from reagent reservoirs to a flow cell. The manifold includes reagent sippers 103 and 104 extending downward in a dimension z from ports in the manifold. The reagent sippers 103 and 104 can be placed into one or more reagent reservoirs (not shown) in a reagent cartridge. The manifold also includes channels 107 fluidly connecting the reagent sipper 103 to a valve 102 and valve 109. The reagent sippers 103 and 104, the channels 107 and the valve 102 mediate fluid communication between the reagent reservoirs and a flow cell (not shown). Valves 102 and 109 may individually, or in conjunction, select sippers 103 or 104, and through channels such as 107, mediate fluid communication between the reagent reservoirs and a flow cell (not shown).

The apparatuses shown in FIGS. 1A and 1B are exemplary. Further exemplary embodiments of the methods and apparatus of the present disclosure that can be used alternatively or additionally to the example of FIGS. 1A and 1B are set forth in further detail below.

Figure 2:
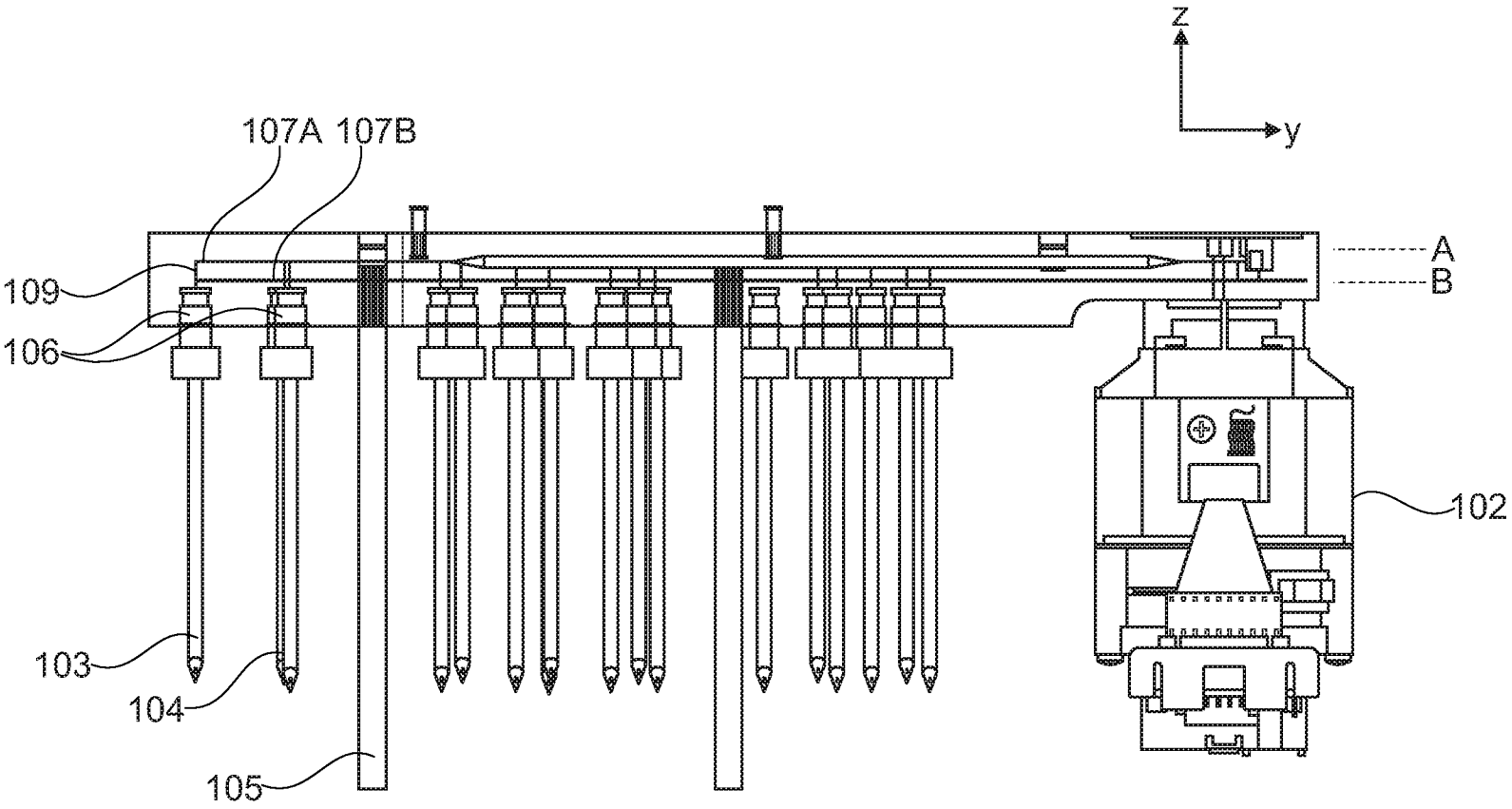
FIG. 2 shows a front perspective view of a manifold assembly having reagent sippers, valves and alignment pints. It also shows sippers of different lengths.

FIG. 2 shows another exemplary manifold assembly having reagent sippers and valves. The manifold has alignment pins 105 protruding downward from the manifold in an axis parallel to the reagent sippers. The alignment pins 105 are longer along the z dimension compared to the reagent sippers, although in alternative embodiments they can also be of equal length or shorter. The alignment pins 105 are configured to engage with one or more corresponding interface slots on a reagent cartridge (not shown). The reagent sippers 103 and 104 are coupled to the manifold via ports 106 that are housed in the manifold body. Reagent sippers 104 are longer in comparison to reagent sippers 103, in order to draw liquid from reagent reservoirs of varying depth that corresponds to the depth of the reagent sipper 103 or 104. In alternative embodiments, sippers 103 and 104 can be of equal lengths, or may switch dominant lengths.

Also shown in FIG. 2 are channels 107A and 107B which reside on separate x-y planes. Separate channels 107A and 107B can originate from a single channel which then bifurcates at a T-junction 109 generating multiple channels residing on separate planes. The manifold directs liquid reagent from one sipper to one or more valves by having the channels which connect to a particular valve 102 reside either, entirely on the same plane A, or a combination of plane A and B, while channels which connect to any other valve may share this characteristic of co-plane or inter-plane origination.

Figure 3:
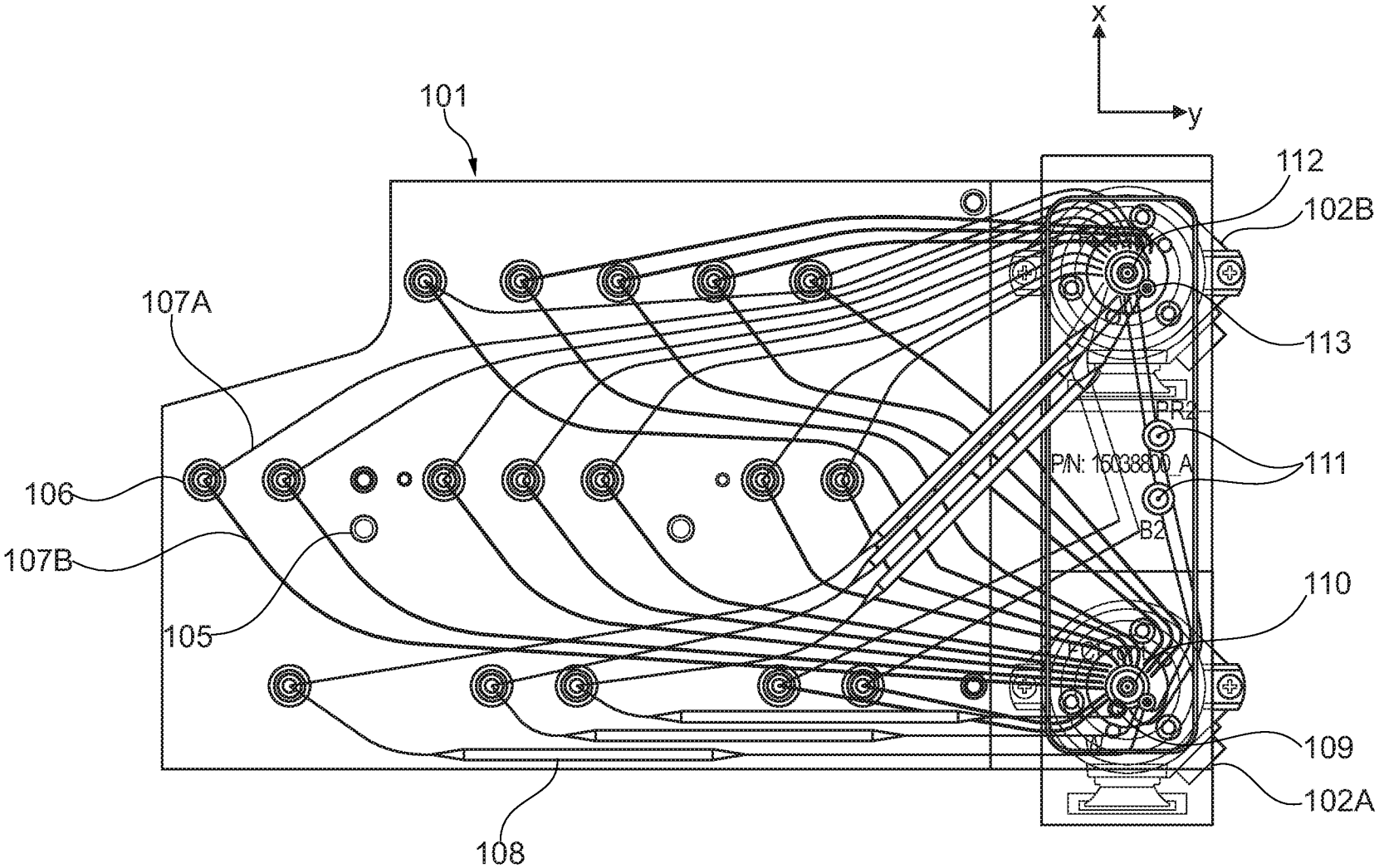
FIG. 3 shows a top view of a manifold assembly displaying one possible layout of fluidic channels within the manifold.

FIG. 3 shows a top view of a manifold assembly 101 displaying one possible layout of fluidic channels within the manifold. Fluidic channels 107A and 107B originate from a single port 106 and connect port 106 to either valve 102A or 102B. Certain channels include a cache reservoir 108 which has sufficient volume to allow a quantity of liquid reagent to flow from a flow cell (not shown) to the cache reservoir 108 such that liquid reagent from the flow cell is not directed back to the reagent reservoir (not shown) after contacting the flow cell. Also shown in FIG. 3 are exemplary positions of one or more alignment pin 105. The manifold assembly shown in FIG. 3 also includes inlet ports 111 for shared buffers. Each of valves 102A and 102B are configured with inlet ports corresponding to each reagent port 106, and with a common out ports 112 and 110 which fluidly connect to a flow cell and a waste port 113 and 109 which fluidly connect to a waste receptacle.

As demonstrated by the exemplary embodiments above, a fluidic system for delivering reagents from a reagent cartridge to a flow cell can include a reagent manifold comprising a plurality of channels configured for fluid communication between a reagent cartridge and an inlet of a flow cell. Use of a manifold in fluidic systems provides several advantages over the use of tubing alone. For example, a manifold with fixed channels reduces the likelihood of error during assembly, such as misplacement of tubing attachments, as well as over- or under-tightening of connections. In addition, a manifold provides ease of maintenance, allowing, for example, quick replacement of an entire unit rather than time-intensive testing and replacement of individual lines.

Figure 4:
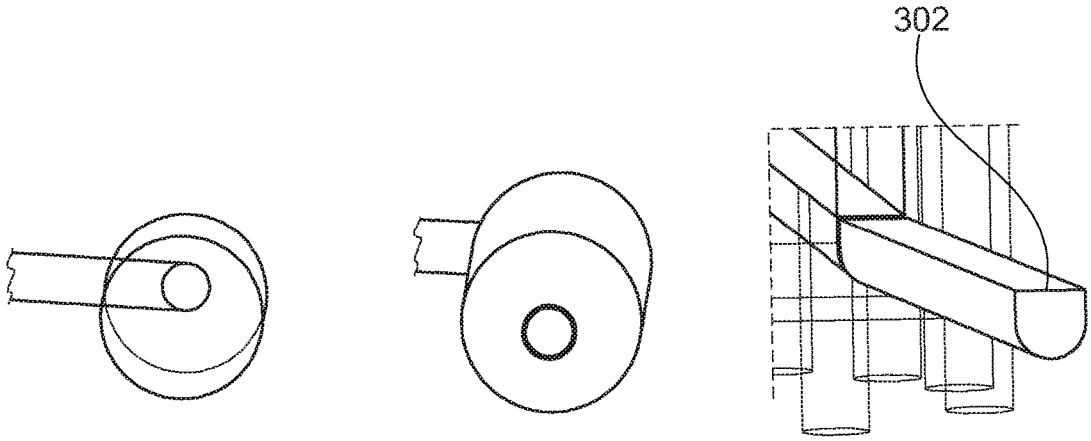
FIG. 4 shows a cross section view of channels within a manifold, including a cross section views of a cache line, and a non-cache fluidic channel.

The one or more of the channels of the manifold can include a fluidic track through a solid material. The track can be of any diameter to allow desired level of fluid transfer through the track. The track can have an inner diameter of, for example, less than 0.1 mm, 0.2 mm, 0.3 mm 0.4 mm, 0.5 mm, 0.6 mm, 0.7 mm, 0.8 mm, 0.9 mm, 1 mm, 2 mm, 3 m, 4 mm, 5 mm, 6 mm, 7 mm, 8 mm, 9 mm or less than 10 mm in diameter. The track configuration can be, for example, straight or curved. Alternatively or additionally, the track can have a combination of curved portions and straight portions. The cross section of the track can be, for example, square, round, "D"-shaped, or any other shape that enables a desired level of fluid transfer through the track. FIG. 4 exemplifies a fluidic track through a manifold body and shows a cross section view of one track 302. The exemplary channel 302 shown in FIG. 4 has a "D" shaped cross section formed by a 0.65 mm diameter half circle fused with an additional 0.65 mm×0.325 mm rectangle.

The channel between the sipper and the valve can be housed entirely within the manifold body. Alternatively or additionally, the channel can include one or more portions that are external to the manifold. For example, tubing such as, for example, flexible tubing can connect a portion of the fluidic track to another portion of the track on the manifold. Alternatively or additionally, flexible tubing can connect a flow cell to fixed fluidic components of the system, including, for example, pumps, valves, sensors and gauges. As an example, flexible tubing can be sued to connect a flow cell or a channel of the present system to a pump such as a syringe pump or a peristaltic pump.

The manifold body can be, for example, made of any suitable solid material that is capable of supporting one or more channels therein. Thus, the manifold body can be a resin such as polycarbonate, polyvinyl chloride, DELRIN® (Polyoxymethylene); HALAR®; PCTFE (PolyChloroTriFluoroEthylene); PEEK™ (Polyetheretherketone); PK (Polyketone); PERLAST®; Polyethylene; PPS (Polyphenylene Sulfide); Polypropylene; Polysulfone; FEP; PFA; High Purity PFA; RADEL® R; 316 Stainless Steel; TEFZEL® ETFE (Ethylene Tetrafluoroethylene); TPX® (Polymethylpentene); Titanium; UHMWPE (Ultra High Molecular Weight Polyethylene); ULTEM® (polyetherimide); VESPEL® or any other suitable solid material that is compatible with the solvents and fluids transported through the channels of the manifold in the embodiments presented herein. The manifold body can be formed from a single piece of material. Alternatively or additionally, the manifold body can be formed from multiple layers that are bonded together. Methods of bonding include, for example, the use of adhesives, gaskets, and diffusion bonding. The channels can be formed in the solid material by any suitable method. For example, channels can be drilled, etched or milled into the solid material. Channels can be formed in the solid material prior to bonding multiple layers together. Alternatively or additionally, channels can be formed after bonding layers together.

Figure 5:
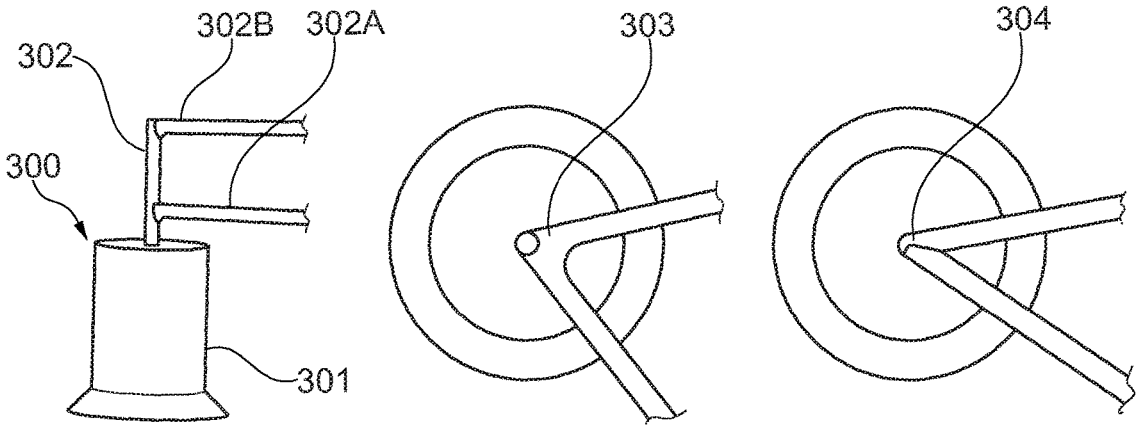
FIG. 5 shows a variety of junctions for connecting a reagent port with two valves.

FIG. 5 shows a variety of junctions 300 for connecting a reagent port 301 with two valves. In each example shown in FIG. 5, a port 301 is fluidly connected to a channel 302 which bifurcates into two channels 302A and 302B with each channel supplying a different valve. In the first configuration, the junction splits fluid flow from port 301 to channels 302A and 302B on separate layers of the manifold. In the second and third configurations shown in FIG. 5, the junction 300 includes a rounded square 303 split within a layer or a full round split 304 within a layer of the manifold.

The manifold assemblies presented here are configured for delivery of liquid reagents from a reagent cartridge to a flow cell. Thus, the manifold can have any number of ports coupled to reagent sippers. More specifically, the number of ports can correspond to the number and configuration of reagent reservoirs in a reagent cartridge. In some embodiments, the manifold comprises at least 2, 3, 4, 5, 6, 7, 8, 9, 10, 11, 12, 13, 14, 15, 16, 17, 18, 19, 20, or at least 30 ports, each port configured to couple a reagent sipper to a channel in fluid communication with the at least one valve.

Figure 10:
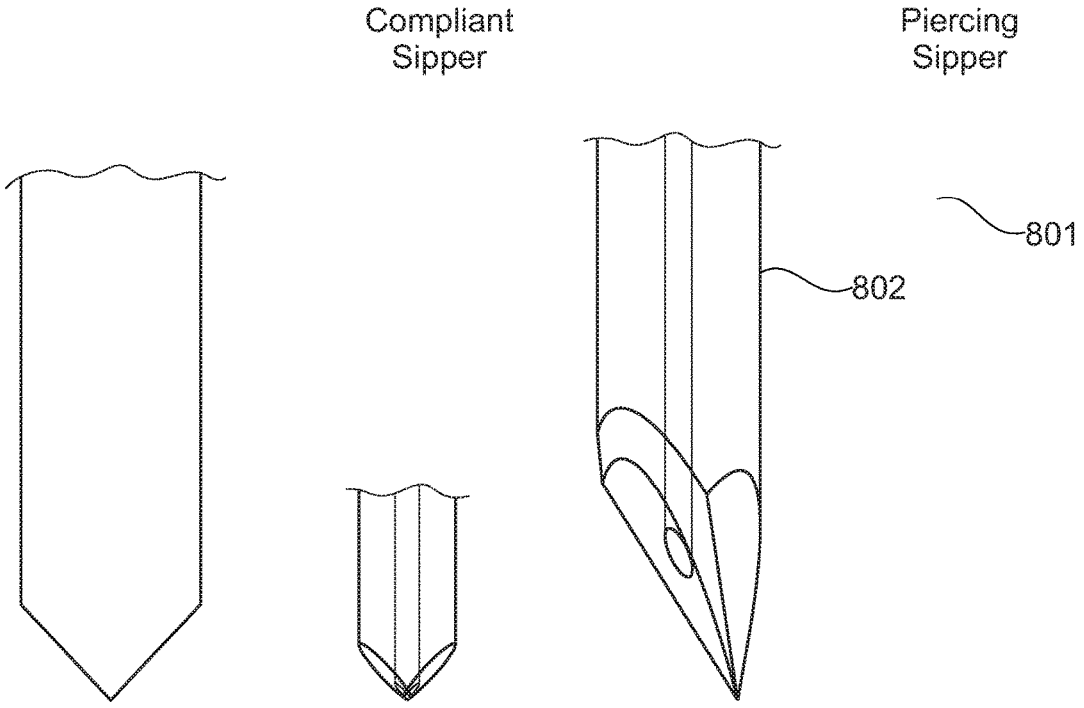
FIG. 10 shows a detailed view of reagent sippers including compliant sippers and a piercing sipper.

The fluidic systems presented herein can also include an array of sipper tubes extending downward along the z dimension from ports in the manifold, each of the reagent sippers configured to be inserted into a reagent reservoir in a reagent cartridge so that liquid reagent can be drawn from the reagent reservoir into the sipper. The reagent sippers can comprise, for example, a tubular body with a proximal end and a distal end. The distal end can taper to a sharp tip that is configured to pierce a film or foil layer used as a seal over a reagent reservoir in a reagent cartridge. Various exemplary sipper tips are shown in FIG. 10. The reagent sippers can be provided with, for example, a single lumen running through the tubular body from the distal to the proximal end. The lumen can be configured to provide fluid communication between the reagent cartridge on one end of the sipper and the reagent manifold on the other end of the sipper. As shown in exemplary FIG. 2, reagent sippers 103 and 104 are coupled to the manifold via ports 106 that are housed in the manifold body.

In some embodiments, as exemplified in FIG. 2, a subset of the reagent sippers is of a length that is shorter than other reagent sippers. For example, the length of the subset can be at least 1, 1.2, 1.3, 1.4, 1.5, 1.6, 1.7, 1.8, 1.9, or at least 2.0 mm shorter than the other reagent sippers. The manifold and reagent sippers can be used in a device having an elevator mechanism configured to move a reagent cartridge bidirectionally along the z dimension such that the reagent sippers are inserted into corresponding wells or reservoirs in the reagent cartridge. In certain embodiments, the reagent wells may be covered with protective foils. Thus, an advantage of providing sippers of varying length is a reduction in the force required by the elevator mechanism to accommodate a foil-piercing force when a reagent cartridge is brought into contact with the piercing sippers. The difference in sipper length can advantageously correspond to the depth of reagent wells in a reagent cartridge, so that each sipper reaches a desired depth in its corresponding reagent well when the sippers and the cartridge are in a fully engaged position.

The sippers can be formed of any suitable material that allows fluid transfer through a lumen and which is compatible with the solvents and fluids transported through the channels of the manifold in the embodiments presented herein. The sippers can be formed from a single tube. Alternatively or additionally, one or more sippers can be made of multiple segments that together form a sipper of a desired length and diameter.

In some embodiments, at least one of the reagent sippers includes a compliant tip configured to flex when the tip impinges upon the bottom of a reagent well in a reagent cartridge. By flexing or deforming, a compliant tip allows the lumen of the sipper to more fully approach or even contact the bottom of the reagent well, thereby reducing or even eliminating the evacuation volume in the reagent well. A compliant tip can be especially advantageous for uptake of sample or reagents where small volumes are used, or in situations where it is desirable for uptake of most or all of the liquid in a reagent reservoir. The body of the sipper having a compliant tip can be made entirely of the same flexible material as the tip. Alternatively or additionally, the body of the sipper can be made of a distinct material than the tip. The compliant tip can be made of any suitable material such that the compliant tip may deform or yield when urged into contact with the bottom of a reagent reservoir. Some suitable materials include polymeric and/or synthetic foams, rubber, silicone and/or elastomers, including thermoplastic polymers such as polyurethane.

The fluidic systems presented herein may also include, for example, pumps and valves that are selectively operable for controlling fluid communication between the reservoirs and the inlet of the flow cell. As exemplified by the manifold assembly shown in FIGS. 2 and 3, channel outlets on the manifold can be configured to connect with corresponding inlet ports on the one or more valves such that each reagent channel is in fluid communication with an inlet port on the valve. Thus, via the reagent channels of the manifold, one or more or each of the inlet ports can be in fluid communication with a reagent sipper. Each of the one or more valves can be configured with a common out port (110, 112) which fluidly connects to an inlet of one or more lanes on a flow cell. Alternatively or additionally, each of the one or more valves can be configured with a waste port (109, 113) fluidly connected to one or more waste receptacles.

In embodiments where the fluidic system comprises at least a first valve and a second valve, each valve can be configured to simultaneously deliver separate reagents across a first channel and a second channel of a flow cell, respectively. Thus, one valve can deliver one reagent to a first flow cell channel while the second valve can simultaneously deliver a different reagent to a second flow cell channel. As shown in exemplary embodiments of FIG. 9, valve A (VA) is fluidly connected to inlet V1 of the flow cell, which is a manifold to deliver reagents to lane 1 and lane 3. Similarly, valve B (VB) is fluidly connected to inlet V2 situated on the opposite end of the flow cell, and which delivers reagents to lane 2 and lane 4. Inlets V1 and V2 are situated on opposite ends of the flow cell and the direction of reagent flow occurs in opposite directions for lanes 1 and 3 compared to lanes 2 and 4.

The fluidic systems described herein can be used advantageously for fluidic manipulation of flow cell channels during nucleic acid sequencing. More specifically, a fluidic system described herein can be operably associated with a detection apparatus in a configuration for detection of nucleic acid features in the flow cell by the detection apparatus. In some embodiments, the detection apparatus can comprise a plurality of microfluorometers, wherein each of the microfluorometers comprises an objective configured for wide-field image detection in an image plane in x and y dimension. The fluidic systems set forth herein are particularly useful with any of the detection apparatus configurations set forth in U.S. patent application Ser. No. 13/766,413 filed on Feb. 13, 2013 and entitled "INTEGRATED OPTO-ELECTRONIC READ HEAD AND FLUIDIC CARTRIDGE USEFUL FOR NUCLEIC ACID SEQUENCING," the content of which is incorporated by reference in its entirety.

As an example, in particular nucleic acid sequencing embodiments, a flow cell that contains a plurality of channels can be fluidically manipulated and optically detected in a staggered fashion. More specifically, the fluidic manipulations can be carried out on a first subset of the channels in the flow cell while optical detection occurs for a second subset of the channels. For example, in one configuration at least four linear channels can be disposed parallel to each other in the flow cell (e.g. channels 1 through 4 can be ordered in sequential rows). Fluidic manipulations can be carried out on every other channel (e.g. channels 1 and 3) while detection occurs for the other channels (e.g. channels 2 and 4). This particular configuration can be accommodated by using a read head having detectors positioned in a spaced apart configuration such that the objectives are directed to every other channel of the flow cell. In this case, valves can be actuated to direct flow of reagents for a sequencing cycle to alternating channels while the channels that are being detected are maintained in a detection state. In this example, a first set of alternating channels can undergo fluidic steps of a first sequencing cycle and a second set of alternating channels undergo detection steps of a second sequencing cycle. Once the fluidic steps of the first cycle are completed and detection steps of the second cycle are completed, the read head can be stepped over (e.g. along the x dimension) to the first set of alternating channels and valves can be actuated to deliver sequencing reagents to the second set of channels. Then detection steps for the first cycle can be completed (in the first set of channels) and fluidic steps for a third cycle can occur (in the second set of channels). The steps can be repeated in this way several times until a desired number of cycles have been performed or until the sequencing procedure is complete.

An advantage of the staggered fluidic and detection steps set forth above is to provide for a more rapid overall sequencing run. In the above example, a more rapid sequencing run will result from the staggered configuration (compared to fluidically manipulating all channels in parallel followed by detection of all channels in parallel) if the time required for fluidic manipulation is about the same as the time required for detection. Of course, in embodiments where the timing for detection steps is not the same as the timing for fluidic steps, the staggered configuration can be changed from every other channel to a more appropriate pattern to accommodate parallel scanning of a subset of channels while another subset of channels undergoes the fluidic steps.

An additional advantage to having fluid flow in opposite directions is to provide a means of comparison of individual microfluorometer performance. For example, where multiple microfluorometers are used per flow cell lane, it can be difficult to distinguish if decreased microfluorometer performance is caused by the detector or from decreased chemistry efficiency from one end of the lane to the other. By having opposing directions of liquid flow, microfluorometer performance across the lanes can be compared, effectively distinguishing whether decreased performance is due to the microfluorometer or not.

Figure 9:
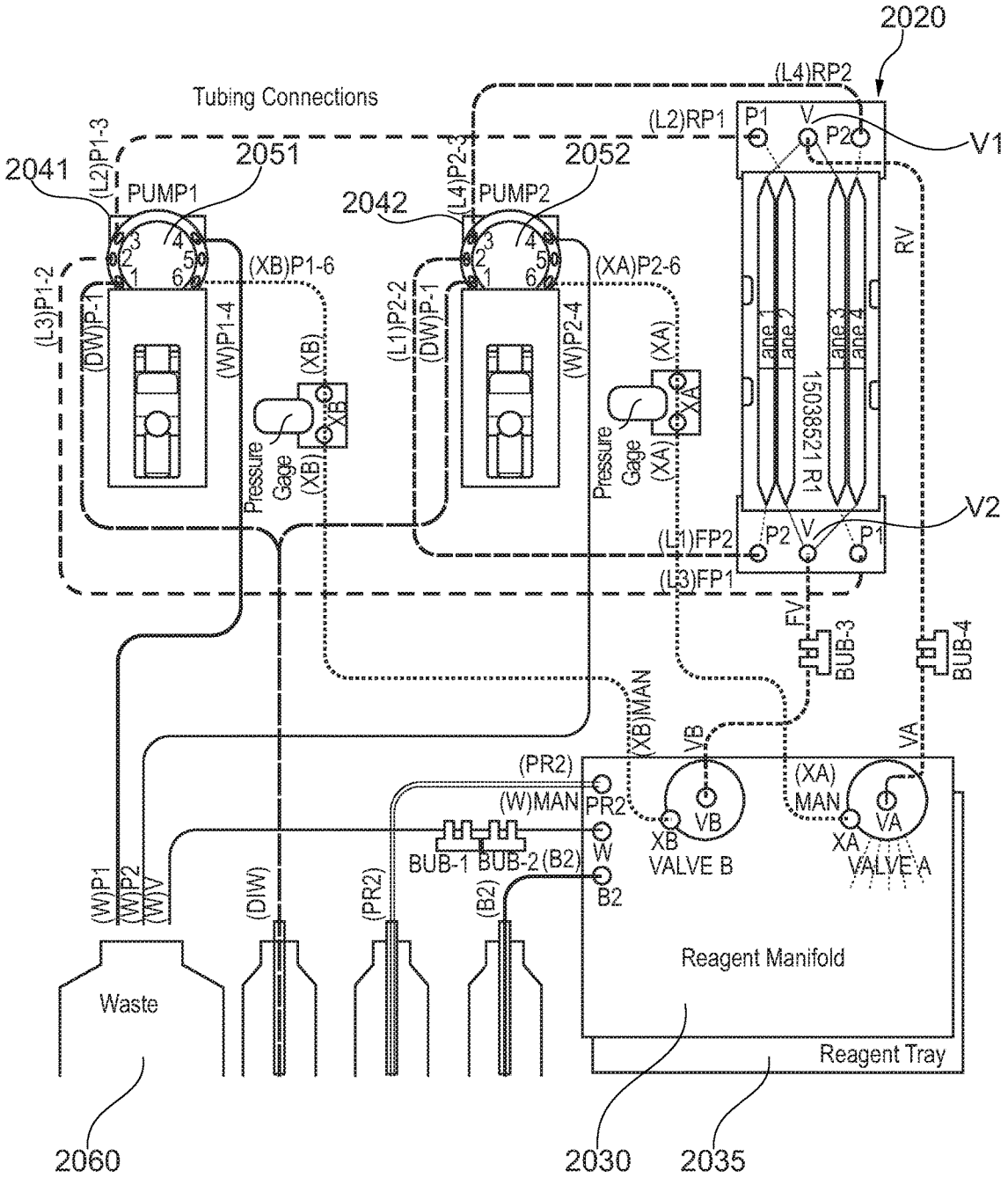
FIG. 9 shows a fluidics map for a fluidic system.

A fluidic map for an exemplary fluidic system is shown in FIG. 9. Flow cell 2020 has four lanes each fluidically connected to one of two individual fluid lines FV and RV that are individually actuated by inlet valves VA and VB. Inlet valve VA and inlet valve VB control the flow of fluid from sample reservoirs, SBS reagent reservoirs and amplification reagent reservoirs in reagent cartridge or tray 2035 fluidically connected to various ports within reagent manifold 2030.

Flow of fluids through the system of FIG. 9 is driven by two separate syringe pumps 2041 and 2042. The syringe pumps are positioned to pull fluids through the fluidic system and each pump can be individually actuated by valves 2051 and 2052. Thus, flow though each channel of the flow cell can be individually controlled by a dedicated pressure source. Valves 2051 and 2052 are also configured to control flow of fluids to waste reservoir 2060.

FIG. 9 exemplifies a fluidic system in which fluids are pulled by the action of downstream syringe pumps. It will be understood that a useful fluidic system can use other types of devices instead of syringe pumps to drive fluids including, for example, positive or negative pressure, peristaltic pump, diaphragm pump, piston pump, gear pump or Archimedes screw. Furthermore, these and other devices can be configured to pull fluids from a downstream position with respect to a flow cell or to push fluids from an upstream position.

FIG. 9 also exemplifies the use of two syringe pumps for four channels of a flow cell. Thus, the fluidic system includes a number of pumps that is less than to the number of channels in use. It will be understood that a fluidic system that is useful in a fluidic cartridge of the present disclosure can have any number of pumps, for example, an equivalent or fewer number of pumps (or other pressure sources) than the number of channels in use. For example, several channels can be fluidically connected to a shared pump and a valve can be used to actuate fluid flow through an individual channel.

The fluidic system exemplified in FIG. 9 also includes a sensor BUB-4 for detecting air bubbles, positioned along the fluid path RV between valve VA and flow cell inlet V1. An additional air bubble sensor BUB-3 is positioned along the fluid path FV between valve VB and flow cell inlet V2. It will be understood that a fluidic line that is useful in a fluidic system of the present disclosure can include any number of air bubble sensors, pressure gauges, and the like. The sensors and/or gauges can be located at any position along any part of the fluid path in the fluidic system. For example, a sensor or gauge can be positioned along a fluidic line between one of the valves and the flow cell. Alternatively or additionally, a sensor or gauge can be positioned along a fluidic line between a reagent reservoir and one of the valves, between a valve and a pump, or between a pump and an outlet or reservoir such as a waste reservoir.

Figure 6:
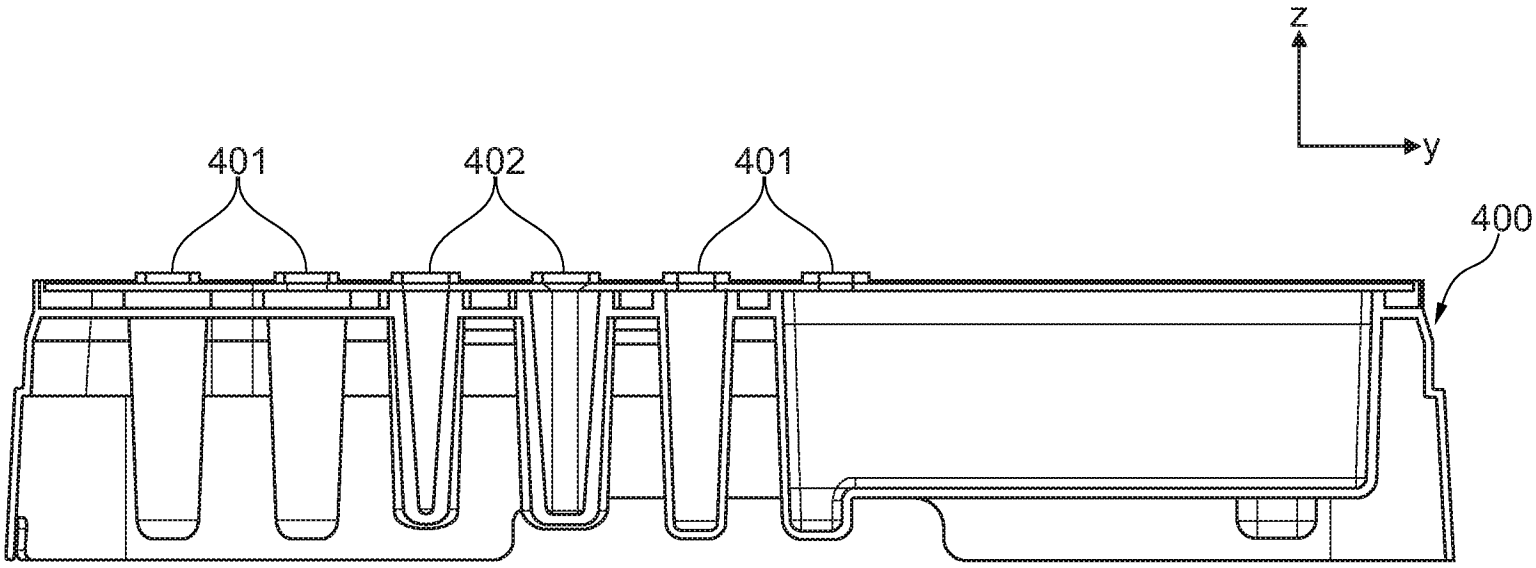
FIG. 6 shows a cross section view of a reagent cartridge having wells of varying depths.

A cross-section of an exemplary reagent cartridge is shown in FIG. 6. The reagent cartridge 400 shown in FIG. 6 includes wells 401 of varying depths along the z dimension compared to those of wells 402. More specifically, the reagent cartridge exemplified in FIG. 6 has wells designed to accommodate the length of a corresponding reagent sipper (not shown) such that each sipper reaches a desired depth in its corresponding reagent well when the sippers and the cartridge are in a fully engaged position. In the reagent cartridge exemplified in FIG. 6, the wells are arranged in row or column along the y dimension, where those wells 401 on the outside of the row or column extend downward further along the z dimension than those wells 402 on the inside of the row or column. Some or all of the wells can be of varying depths. Alternatively or additionally, some or all of the wells can be of the same depth. When the sippers and the cartridge are in a fully engaged position, the penetration depth of any sipper tip (i.e., the distance from the bottom surface of the well to the end of the sipper tip) can be equivalent to the penetration depth of any other sipper tip in any other given well in the reagent cartridge. The penetration depth of any sipper tip need not be the same as the penetration depth of any other given well in the reagent cartridge. Where at least some reagent wells have a different well depth, the well depth can be, for example, at least 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or at least 2.0 mm shorter than the other reagent sippers. Similarly, when the sippers and the cartridge are in a fully engaged position, the penetration depth of any sipper tip can be at least 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or at least 2.0 mm different than the penetration depth of any other sipper tip in the reagent cartridge.

Figure 8:
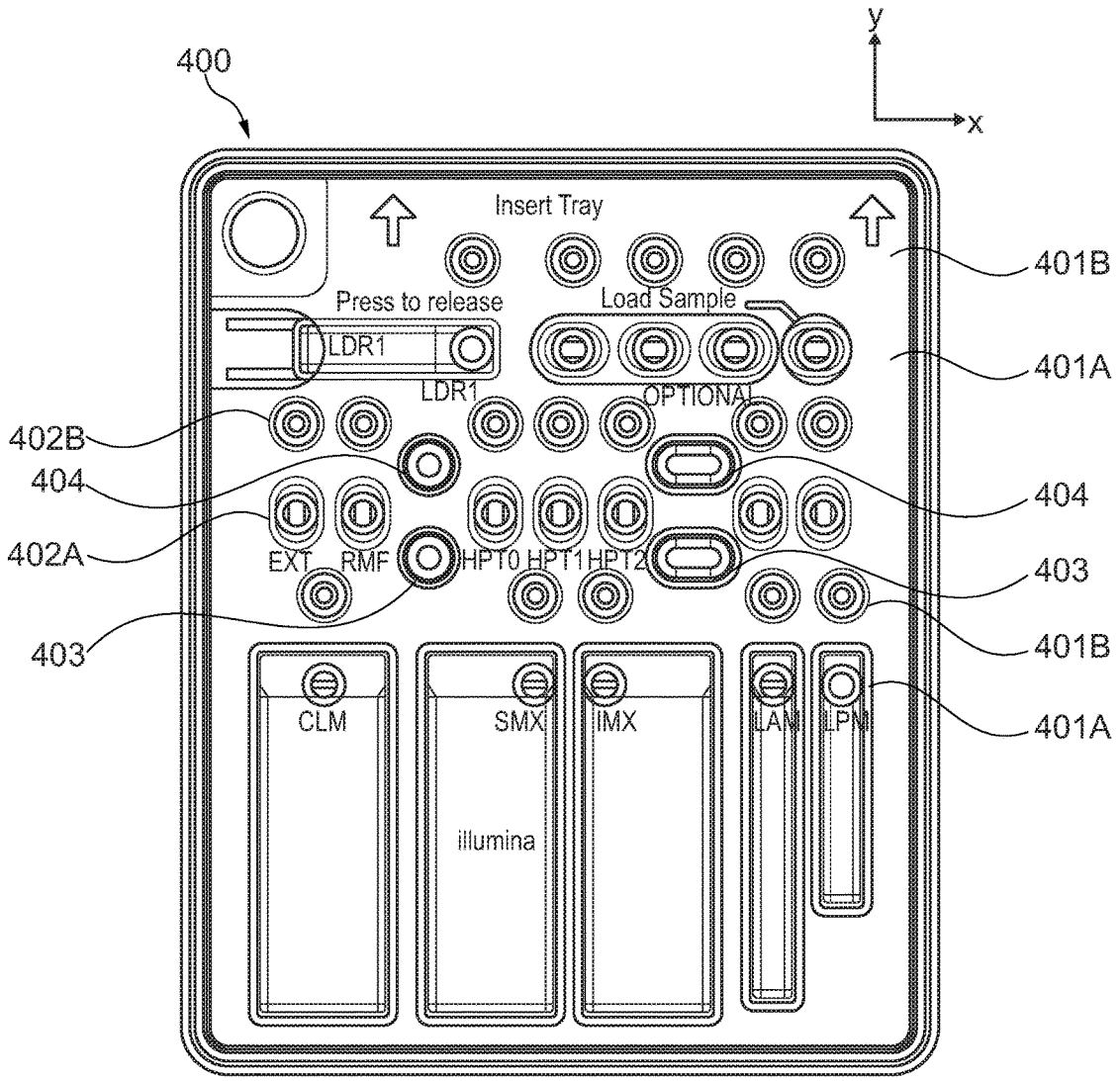
FIG. 8 shows a top view of a reagent tray interface having reagent wells and interface slots for alignment pins.

A top view of an exemplary reagent tray interface having reagent wells and interface slots for alignment pins is shown in FIG. 8. As shown in the exemplary reagent cartridge 400 in FIG. 8, the cartridge includes a plurality of reagent reservoirs 401A, 401B, 402A and 402B. The reagent reservoirs in FIG. 8 are arranged in x and y dimensions into rows. Also shown in FIG. 8, the cartridge includes interface slots 403 and 404 configured to engage with corresponding alignment pins of a manifold assembly (not shown). The cartridge may also include protective foil covering any number of the reagent wells or reservoirs, which can be pierced by piercing sippers when the cartridge is brought into contact with the piercing sippers.

The reagent cartridges presented herein can include any number of reagent reservoirs or wells. The reagent reservoirs or wells can be arranged in any format along the x and y dimensions to facilitate transport and storage of reagents in the cartridge. Alternatively or additionally, reagent reservoirs or wells can be arranged in any format along the x and y dimensions suitable for interaction with an array of sipper tubes extending downward along the z dimension from ports in the manifold. More specifically, the reagent reservoirs or wells can be arranged in any format suitable for simultaneously engaging a matrix of reagent sippers such that liquid reagent can be drawn from the reagent reservoir into the sippers.

Not all reagent wells need interact simultaneously with all sipper tubes of a manifold assembly. For example, the reagent cartridge can include a subset of one or more reagent reservoirs or wells that are configured to remain in a non-interacting state while other reservoirs or wells are engaged by an array of sipper tubes. As one example, a cartridge presented herein can comprises a plurality of wash reservoirs arranged in a configuration corresponding to the plurality of reagent reservoirs, whereby wash reservoirs are configured to simultaneously engage the reagent sippers when the reagent sippers are not engaged with the reagent reservoirs so that wash buffer can be drawn from the wash reservoirs into the sippers. An exemplary embodiment is presented in FIG. 8, which shows a row of reagent wells 401A. The cartridge also includes a row of corresponding wells 401B which retains the same orientation in the x dimension with respect to each other, but which are offset in they dimension from wells 401A. The offset wells 401B can include a wash buffer, for example, provided for rinsing sipper tubes and fluidic lines after using one cartridge and before using another cartridge.

Alternatively or additionally, other reservoirs that are empty, or which hold buffer, sample or other reagents can be present on the cartridge. The additional reservoirs can, but need not interact with a sipper tube. For example, a reservoir can be configured to be filled with waste or overflow reagent or buffer over the course of cartridge use. Such a reservoir may be accessed, for example via a port that does not interface with a sipper tube.

To facilitate correct alignment of cartridge reservoirs with corresponding sipper tubes, alignment slots can be positioned in the cartridge. For example, in particular embodiments where an array of sipper tubes is removed from one set of reservoirs and translocated to another set of reagent or wash reservoirs, alignment slots can be positioned in the cartridge to ensure correct alignment of the array of reagent sippers with one or both sets of reservoirs. As shown in FIG. 8, the exemplary cartridge includes alignment slots 404 which retain the same orientation in the x dimension, but which are offset in they dimension with respect to corresponding alignment slot 403. A cartridge of the embodiments presented herein can have any number of alignment slots which provide suitable alignment with the features of a fluidic assembly. For example, a cartridge can include 0, 1, 2, 3, 4, 5, 6, 7, 8, 9, 10 or more alignment slots configured to engage with corresponding alignment pins of the fluidic system so that reagent sippers of the fluidic system are positioned in alignment with the reagent and/or wash reservoirs.

In particular embodiments a fluidic system can be configured to allow re-use of one or more reagents. For example, the fluidic system can be configured to deliver a reagent to a flow cell, then remove the reagent from the flow cell, and then re-introduce the reagent to the flow cell. One configuration is exemplified in FIG. 7A, which shows a top view of cache lines in a manifold assembly. As shown in the schematic in the top portion of FIG. 7A, a reagent cache can be used to maintain a concentration gradient from most used to least used (fresh) reagent. In some embodiments, the cache reservoir can be configured to reduce mixing of fluid within the cache reservoir, thereby maintaining a gradient of liquid reagent along the length of the reservoir from the end proximal to the flow cell to the end distal to the flow cell. As reagent is delivered back to the flow cell from the cache reservoir, the gradient is maintained such that reagent flowed across the flow cell forms a gradient from most used to least used (fresh) reagent.

Figure 7A:
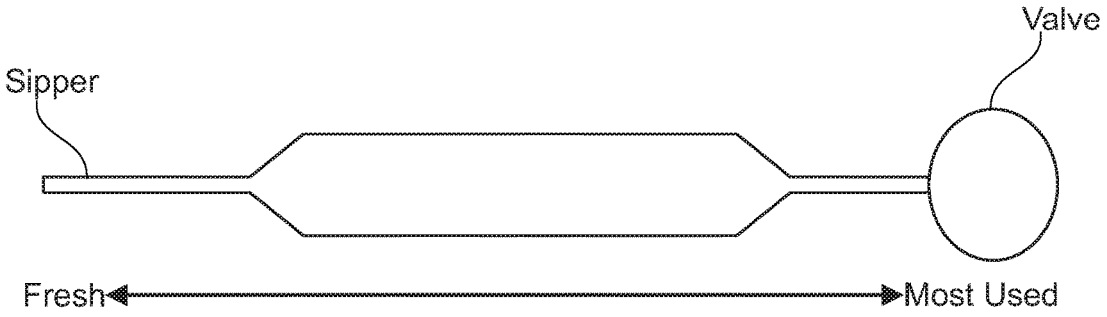
FIG. 7A shows a simplified top view of cache lines in a manifold assembly according to one embodiment.
Figure 7A:
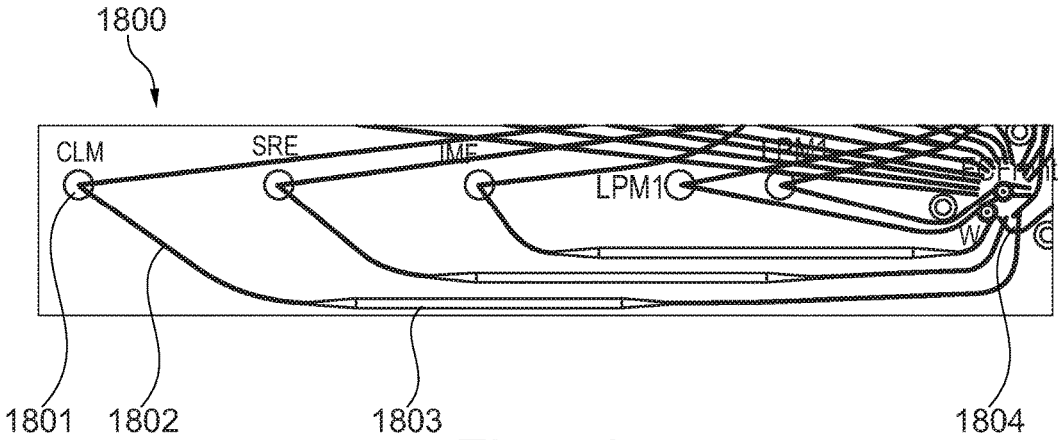

As exemplified the diagram in the bottom portion of FIG. 7A, manifold fluidics can be configured such that a reagent reservoir is in fluid communication with the input port of a flow cell (not shown) via valve inlet 1804. Valve 1804 controls flow of fluids between flow cell (not shown) and each of CLM reservoir, SRE reservoir, IMF reservoir, and LAM1 and LPM1 reservoirs. Channel 1802 fluidly connects CLM reservoir via port 1801 with valve inlet 1804. A portion of channel 1802 includes a reagent cache 1803 configured to hold a volume of reagent equivalent to the volume of one or more lanes of flow cell (not shown). The increased volume of reagent cache 1803 compared with other portions of channel 1802 allows used reagent to be stored for re-use while maintaining a stock of unused reagent in the reagent reservoir, thereby avoiding contaminating the unused reagent stock in the reagent reservoir with used reagent.

The configuration shown in FIG. 7A is exemplary. Other configurations are possible as well to achieve re-use. For example, one or more of the cache reservoirs can have a volume that is 5%, 10%, 15%, 20%, 25%, 30%, 35%, 40%, 45%, 50%, 55%, 60%, 65%, 70%, 75%, 80%, 85%, 90%, 95%, 100%, 150%, 200%, 250%, 300%, 350%, 400%, 450%, 500%, 550%, 600%, 650%, 700%, 750%, 800%, 850%, 900%, 950%, 1000%, 1500%, 2000%, 2500%, 3000% or more of the volume of a flow cell channel in fluid communication with the cache reservoir. Alternatively or additionally, the cache reservoir can comprise sufficient volume to allow a quantity of liquid reagent in one or more flow cell channels to flow to the cache reservoir such that the liquid reagent from the flow cell is not directed back to the reagent reservoir after contacting the flow cell. For example, the quantity of liquid reagent can comprise 5%, 10%, 15%, 20%, 25%, 30%, 35%, 40%, 45%, 50%, 55%, 60%, 65%, 70%, 75%, 80%, 85%, 90%, 95%, 100%, 150%, 200%, 250%, 300%, 350%, 400%, 450%, 500%, 550%, 600%, 650%, 700%, 750%, 800%, 850%, 900%, 950%, 1000%, 1500%, 2000%, 2500%, 3000% or more of the liquid reagent in one or more flow cell channels.

A cache reservoir as presented herein can be configured to reduce mixing of fluid within the cache reservoir. In some such embodiments, reduced mixing can thereby maintain a gradient of liquid reagent along the length of the reservoir from the end proximal to the flow cell to the end distal to the flow cell. Alternatively or additionally, a cache reservoir as presented herein can comprise one or more mixing elements configured to promote mixing of fluid within the cache reservoir. Any suitable active or passive mixing element can be used in such embodiments. For example, the mixing element could comprise baffle elements, curved structures or any other passive or active structural or fluidic feature configured to promote mixing as fluid is transported across a cache reservoir. Alternatively or additionally, any suitable pump, rotor, blade, inlet and the like can be used for active mixing within a cache reservoir.

A cache reservoir as presented herein can have any shape, volume and length that is suitable for the purposes of a cache reservoir. In specific embodiments, cache reservoirs of any shape, volume and/or length can be used in the fluidic systems presented herein which allow a quantity of liquid reagent in one or more flow cell channels to flow to the cache reservoir such that the liquid reagent from the flow cell is not directed back to the reagent reservoir after contacting the flow cell. For example, a cache reservoir can comprise a serpentine channel. By way of another example, a cache reservoir can comprise a channel of cylindrical or noncylindrical shape. Further, any number of fluidic channels in the fluidic system presented herein can include one or more individual cache reservoirs.

A cache reservoir as presented herein can be in fluid communication with a pump configured to move liquid reagent from the cache reservoir to the flow cell and from the flow cell back to the cache reservoir, wherein ingress of reagent to the flow cell and egress of reagent from the flow cell occur through the same port of the flow cell. Alternatively or additionally, ingress of reagent to the flow cell and egress of reagent from the flow cell may occur through distinct ports of the flow cell and still achieve reagent re-use. For example, the fluidic systems presented herein can make use of any of the reuse reservoirs and configurations described in connection with the apparatus configurations set forth in U.S. patent application Ser. No. 13/766,413 filed on Feb. 13, 2013 and entitled "INTEGRATED OPTOELECTRONIC READ HEAD AND FLUIDIC CARTRIDGE USEFUL FOR NUCLEIC ACID SEQUENCING," the content of which is incorporated by reference in its entirety.

Figure 7B:
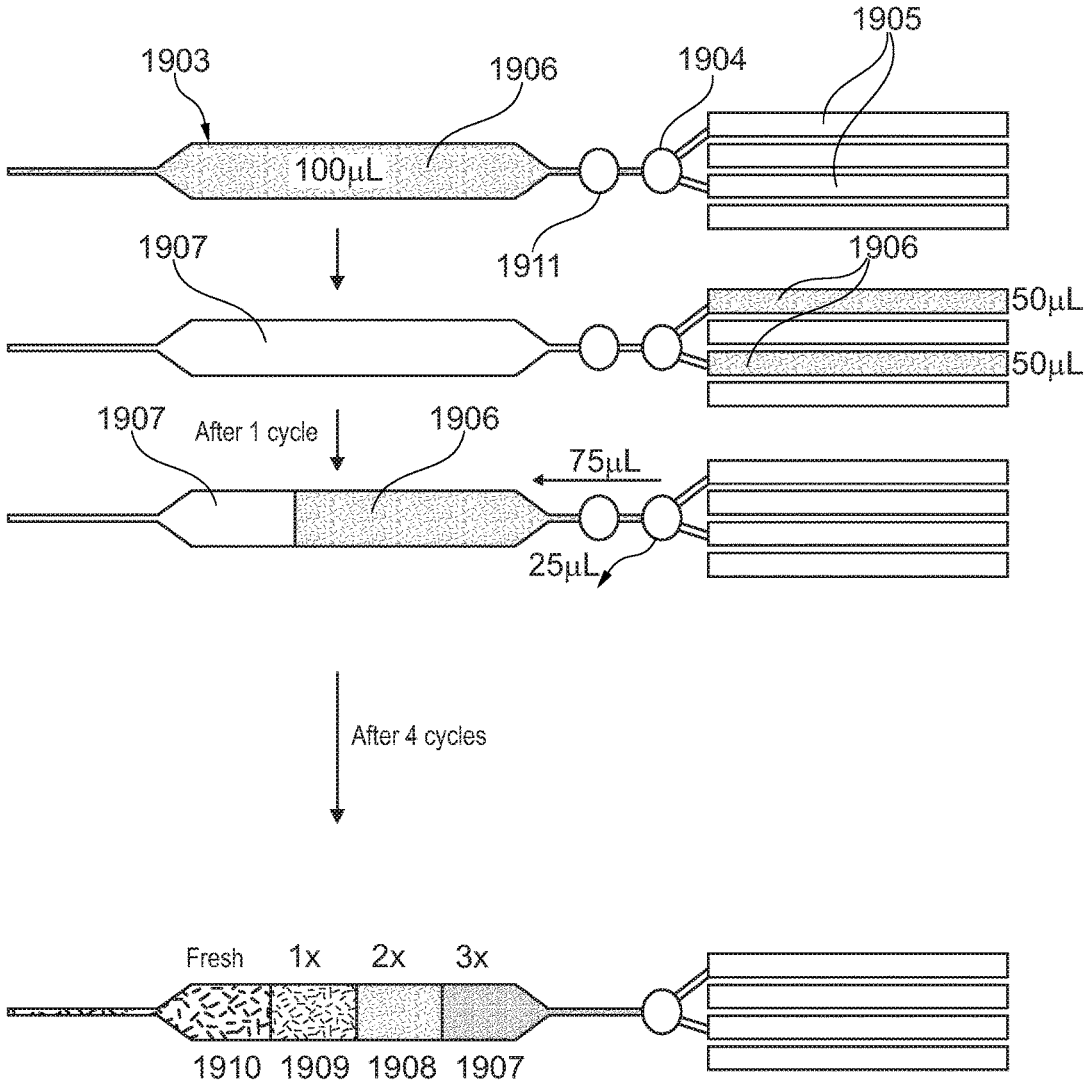
FIG. 7B shows various stages of reagent re-use in a method that utilizes reciprocal flow of reagent from a cache line to a flow cell, followed by partial refilling of the cache line from the flow cell.

The schematic of FIG. 7B sets forth an exemplary illustration of a re-use method presented herein that utilizes reciprocal flow of reagent from a cache line to a flow cell, followed by partial refilling of the cache line from the flow cell. In the state shown in the top panel of FIG. 7B, cache reservoir 1903 containing 100 μL of reagent 1906 is in fluid communication with flow cell lanes 1905 via splitter 1904 and valve 1911. Valve 1904 is actuated to allow reagent 1906 to flow to flow cell lanes 1905. At the same time, fresh reagent 1907 is pulled from reagent reservoir to fill void left in cache reservoir 1903. After use of the reagent on the flow cell, valve 1911 directs a portion (75 μL) of used reagent 1906 back into cache reservoir 1903. Another portion (25 μL) of used reagent 1906 is diverted by valve 1911 to a waste receptacle. At the end of cycle 1, cache reservoir 1903 has a gradient with 25 μL fresh reagent 1907 and 75 μL used reagent 1906 across the length of the cache reservoir. The cycle of reciprocal flow of reagent from cache reservoir to flow cell and back to cache reservoir is repeated, with a portion (25 μL) of used reagent 1906 diverted at each cycle by valve 1911 to a waste receptacle and the remainder of used reagent 1906 is flowed back to cache reservoir 1903. At the end of four such repeated cycles, the cache reservoir 1903 contains 25 μL fresh reagent 1910, 25 μL of reagent that has been used once 1909, 25 μL of reagent that has been used twice 1908, and 25 μL of reagent that has been used three times 1907.

The configurations shown in FIG. 7A and FIG. 7B are exemplary. Other configurations are possible as well to achieve re-use of one or more of the reagents used in a particular process. It will be understood that in some reagent re-use configurations, fluidic configurations for reagent re-use will only be used for a subset of the reagents used in a particular process. For example, a first subset of the reagents may be robust enough to be re-used whereas a second subset may be prone to contamination, degradation or other unwanted effects after a single use. Accordingly, the fluidic system can be configured for re-use of the first subset of reagents, whereas the fluidics for the second set of reagents will be configured for single use.

A particular reagent can be re-used any number of times desired to suit a particular process. For example, one or more of the reagents exemplified herein, described in a reference cited herein, or otherwise known for use in a process set forth herein can be re-used at least 2, 3, 4, 5, 10, 25, 50 or more times. Indeed any of a variety of desired regents can be re-used for at least as many times. Any portion of a particular reagent can be diverted back to a cache reservoir for re-use. For example, one or more of the reagents exemplified herein, described in a reference cited herein, or otherwise known for use in a process set forth herein can have 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100% of the volume of reagent on one or more flow cell lanes directed back to a cache reservoir for subsequent re-use. Alternatively or additionally, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100% of the volume of reagent on one or more flow cell lanes can be diverted to a waste receptacle or otherwise removed from subsequent use on a flow cell.

Fluidic configurations and methods for reagent re-use, although exemplified for a nucleic acid sequencing process, can be applied to other processes, in particular processes that involve repeated cycles of reagent delivery. Exemplary processes include sequencing of polymers such as polypeptides, polysaccharides or synthetic polymers and also include synthesis of such polymers.

As demonstrated by the exemplary embodiments above, a method of reagent re-use can include steps of: a) drawing a liquid reagent from a reagent reservoir into a cache reservoir, the cache reservoir in fluid communication with the reagent reservoir and at least one channel of a flow cell; b) transporting the reagent from the cache reservoir onto the at least one channel of the flow cell; c) transporting at least 30%, 40%, 50%, 60%, 70%, 80%, 90%, or 100% of the reagent on the flow cell channel to the cache reservoir such that the liquid reagent from the flow cell is not directed back to the reagent reservoir after contacting the flow cell; d) repeating steps b) and c) to achieve re-use of the liquid reagent on the flow cell. The one or more of the cache reservoirs can be in fluid communication with a pump configured to move liquid reagent from the cache reservoir to the flow cell and from the flow cell back to the cache reservoir, such that ingress of reagent to the flow cell and egress of reagent from the flow cell occur through the same port of the flow cell. Alternatively or additionally, ingress of reagent to the flow cell and egress of reagent from the flow cell may occur through distinct ports of the flow cell and still achieve reagent re-use. In some embodiments, reagent from the flow cell that is not transported to the cache reservoir in step c) can be diverted. As an example, reagent from the flow cell that is not transported to the cache reservoir can be transported to a waste reservoir. Transport of reagent in one or both of steps b) and c) can be performed via a valve which fluidly connects the cache reservoir and the flow cell. Transport of reagent in one or both of steps b) and c) can be performed, for example with fluid flow in a single direction, or can be performed with reciprocating flow.

Embodiments of the present fluidic systems and methods find particular use for nucleic acid sequencing techniques. For example, sequencing-by-synthesis (SBS) protocols are particularly applicable. In SBS, extension of a nucleic acid primer along a nucleic acid template is monitored to determine the sequence of nucleotides in the template. The underlying chemical process can be polymerization (e.g. as catalyzed by a polymerase enzyme) or ligation (e.g. catalyzed by a ligase enzyme). In a particular polymerase-based SBS embodiment, fluorescently labeled nucleotides are added to a primer (thereby extending the primer) in a template dependent fashion such that detection of the order and type of nucleotides added to the primer can be used to determine the sequence of the template. A plurality of different templates can be subjected to an SBS technique on a surface under conditions where events occurring for different templates can be distinguished. For example, the templates can be present on the surface of an array such that the different templates are spatially distinguishable from each other. Typically the templates occur at features each having multiple copies of the same template (sometimes called "clusters" or "colonies"). However, it is also possible to perform SBS on arrays where each feature has a single template molecule present, such that single template molecules are resolvable one from the other (sometimes called "single molecule arrays").

Flow cells provide a convenient substrate for housing an array of nucleic acids. Flow cells are convenient for sequencing techniques because the techniques typically involve repeated delivery of reagents in cycles. For example, to initiate a first SBS cycle, one or more labeled nucleotides, DNA polymerase, etc., can be flowed into/through a flow cell that houses an array of nucleic acid templates. Those features where primer extension causes a labeled nucleotide to be incorporated can be detected, for example, using methods or apparatus set forth herein. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary sequencing techniques are described, for example, in Bentley et al., Nature 456:53-59 (2008), WO 04/018497; U.S. Pat. No. 7,057,026; WO 91/06678; WO 07/123744; U.S. Pat. No. 7,329,492; U.S. Pat. No. 7,211,414; U.S. Pat. No. 7,315,019; U.S. Pat. No. 7,405,281, and US 2008/0108082, each of which is incorporated herein by reference.

For the nucleotide delivery step of an SBS cycle, either a single type of nucleotide can be delivered at a time, or multiple different nucleotide types (e.g. A, C, T and G together) can be delivered. For a nucleotide delivery configuration where only a single type of nucleotide is present at a time, the different nucleotides need not have distinct labels since they can be distinguished based on temporal separation inherent in the individualized delivery. Accordingly, a sequencing method or apparatus can use single color detection. For example, a microfluorometer or read head need only provide excitation at a single wavelength or in a single range of wavelengths. Thus, a microfluorometer or read head need only have a single excitation source and multiband filtration of excitation need not be necessary. For a nucleotide delivery configuration where delivery results in multiple different nucleotides being present in the flow cell at one time, features that incorporate different nucleotide types can be distinguished based on different fluorescent labels that are attached to respective nucleotide types in the mixture. For example, four different nucleotides can be used, each having one of four different fluorophores. In one embodiment the four different fluorophores can be distinguished using excitation in four different regions of the spectrum. For example, a microfluorometer or read head can include four different excitation radiation sources. Alternatively a read head can include fewer than four different excitation radiation sources but can utilize optical filtration of the excitation radiation from a single source to produce different ranges of excitation radiation at the flow cell.

In some embodiments, four different nucleotides can be detected in a sample (e.g. array of nucleic acid features) using fewer than four different colors. As a first example, a pair of nucleotide types can be detected at the same wavelength, but distinguished based on a difference in intensity for one member of the pair compared to the other, or based on a change to one member of the pair (e.g. via chemical modification, photochemical modification or physical modification) that causes apparent signal to appear or disappear compared to the signal detected for the other member of the pair. As a second example, three of four different nucleotide types can be detectable under particular conditions while a fourth nucleotides type lacks a label that is detectable under those conditions. In an SBS embodiment of the second example, incorporation of the first three nucleotide types into a nucleic acid can be determined based on the presence of their respective signals, and incorporation of the fourth nucleotide type into the nucleic acid can be determined based on absence of any signal. As a third example, one nucleotide type can be detected in two different images or in two different channels (e.g. a mix of two species having the same base but different labels can be used, or a single species having two labels can be used or a single species having a label that is detected in both channels can be used), whereas other nucleotide types are detected in no more than one of the images or channels. In this third example, comparison of the two images or two channels serves to distinguish the different nucleotide types.

The three exemplary configurations in the above paragraph are not mutually exclusive and can be used in various combinations. An exemplary embodiment is an SBS method that uses reversibly blocked nucleotides (rbNTPs) having fluorescent labels. In this format, four different nucleotide types can be delivered to an array of nucleic acid features that are to be sequenced and due to the reversible blocking groups one and only one incorporation event will occur at each feature. The nucleotides delivered to the array in this example can include a first nucleotide type that is detected in a first channel (e.g. rbATP having a label that is detected in the first channel when excited by a first excitation wavelength), a second nucleotide type that is detected in a second channel (e.g. rbCTP having a label that is detected in the second channel when excited by a second excitation wavelength), a third nucleotide type that is detected in both the first and the second channel (e.g. rbTTP having at least one label that is detected in both channels when excited by the first and/or second excitation wavelength) and a fourth nucleotide type that lacks a label that is detected in either channel (e.g. rbGTP having no extrinsic label).

Once the four nucleotide types have been contacted with the array in the above example, a detection procedure can be carried out, for example, to capture two images of the array. The images can be obtained in separate channels and can be obtained either simultaneously or sequentially. A first image obtained using the first excitation wavelength and emission in the first channel will show features that incorporated the first and/or third nucleotide type (e.g. A and/or T). A second image obtained using the second excitation wavelength and emission in the second channel will show features that incorporated the second and/or third nucleotide type (e.g. C and/or T). Unambiguous identification of the nucleotide type incorporated at each feature can be determined by comparing the two images to arrive at the following: features that show up only in the first channel incorporated the first nucleotide type (e.g. A), features that show up only in the second channel incorporated the second nucleotide type (e.g. C), features that show up in both channel incorporated the third nucleotide type (e.g. T) and features that don't show up in either channel incorporated the fourth nucleotide type (e.g. G). Note that the location of the features that incorporated G in this example can be determined from other cycles (where at least one of the other three nucleotide types is incorporated). Exemplary apparatus and methods for distinguishing four different nucleotides using detection of fewer than four colors are described for example in U.S. Pat. App. Ser. No. 61/538,294, which is incorporated herein by reference.

In some embodiments, nucleic acids can be attached to a surface and amplified prior to or during sequencing. For example, amplification can be carried out using bridge amplification to form nucleic acid clusters on a surface. Useful bridge amplification methods are described, for example, in U.S. Pat. No. 5,641,658; US 2002/0055100; U.S. Pat. No. 7,115,400; US 2004/0096853; US 2004/0002090; US 2007/0128624; or US 2008/0009420, each of which is incorporated herein by reference. Another useful method for amplifying nucleic acids on a surface is rolling circle amplification (RCA), for example, as described in Lizardi et al., Nat. Genet. 19:225-232 (1998) and US 2007/0099208 A1, each of which is incorporated herein by reference. Emulsion PCR on beads can also be used, for example as described in Dressman et al., Proc. Natl. Acad. Sci. USA 100:8817-8822 (2003), WO 05/010145, US 2005/0130173 or US 2005/0064460, each of which is incorporated herein by reference.

As set forth above, sequencing embodiments are an example of a repetitive process. The methods of the present disclosure are well suited to repetitive processes. Some embodiments are set forth below and elsewhere herein.

Accordingly, provided herein are sequencing methods that include (a) providing a fluidic system comprising (i) a flow cell comprising an optically transparent surface, (ii) a nucleic acid sample, (iii) a plurality of reagents for a sequencing reaction, and (iv) a fluidic system for delivering the reagents to the flow cell; (b) providing a detection apparatus comprising (i) a plurality of microfluorometers, wherein each of the microfluorometers comprises an objective configured for wide-field image detection in an image plane in x and y dimensions, and (ii) a sample stage; and (c) carrying out fluidic operations of a nucleic acid sequencing procedure in the cartridge and detection operations of the nucleic acid sequencing procedure in the detection apparatus, wherein (i) the reagents are delivered to the flow cell by the fluidic system, (ii) wide-field images of the nucleic acid features are detected by the plurality of microfluorometers, and (iii) at least some reagents are removed from the flow cell to a cache reservoir.

Throughout this application various publications, patents and/or patent applications have been referenced. The disclosure of these publications in their entireties is hereby incorporated by reference in this application.

The term comprising is intended herein to be open-ended, including not only the recited elements, but further encompassing any additional elements.

A number of embodiments have been described. Nevertheless, it will be understood that various modifications may be made. Accordingly, other embodiments are within the scope of the following claims.

What is claimed is:

1. A method of reagent re-use comprising:

a) drawing a liquid reagent from a reagent reservoir into a cache reservoir, the cache reservoir in fluid communication with the reagent reservoir and at least one channel of a flow cell;

b) transporting the liquid reagent from the cache reservoir onto the at least one channel of the flow cell;

c) transporting at least 30%[, 40%, 50%, 60%, 70%, 80%, or 90%] of the liquid reagent on the flow cell channel to the cache reservoir such that the liquid reagent from the flow cell is not directed back to the reagent reservoir after contacting the flow cell *and maintaining a gradient of the transported at least 30% of the liquid reagent and fresh liquid within the cache reservoir*; and d) repeating at least b) to achieve re-use of the liquid reagent on the flow cell.

2. The method of claim 1, comprising transporting the liquid reagent from the cache reservoir onto the at least one channel of the flow cell through a valve coupled between the cache reservoir and the flow cell.

3. The method of claim 1, comprising, after c), diverting a portion of liquid reagent to waste.

4. The method of claim 1, comprising repeating b) and c) at least once.

5. The method of claim 1, comprising mixing the liquid reagent within the cache reservoir.

[6. The method of claim 1, comprising maintaining a gradient of used and fresh liquid reagents within the cache reservoir.]

7. A method of reagent re-use comprising:

a) drawing a liquid reagent from a reagent reservoir into a cache reservoir, the cache reservoir in fluid communication with the reagent reservoir and at least one channel of a flow cell;

b) transporting the liquid reagent from the cache reservoir onto the at least one channel of the flow cell;

c) transporting at least a portion of the liquid reagent on the flow cell channel to the cache reservoir such that the liquid reagent from the flow cell is not directed back to the reagent reservoir after contacting the flow cell *and maintaining a gradient of the transported portion of the liquid reagent and fresh liquid reagent within the cache reservoir*;

d) diverting a portion of the liquid reagent from the cache reservoir to waste; and e) repeating at least b) to achieve re-use of the liquid reagent on the flow cell.

8. The method of claim 7, comprising repeating b), c), and d) at least once.

9. The method of claim 7, comprising repeating b), c), and d) multiple times.

10. The method of claim 7, comprising transporting the liquid reagent from the cache reservoir onto the at least one channel of the flow cell through a valve coupled between the cache reservoir and the flow cell.

11. The method of claim 7, comprising mixing the liquid reagent within the cache reservoir.

[12. The method of claim 7, comprising maintaining a gradient of used and fresh liquid reagents within the cache reservoir.]

13. A system comprising:

a reagent reservoir;

a flow cell;

a manifold coupled between the reagent reservoir and the flow cell and comprising a cache reservoir configured to receive liquid reagent from the reagent reservoir, and configured to provide a volume of the liquid reagent into a channel of the flow cell, and configured to receive at least a portion of the liquid reagent back from the flow cell for re-use in the flow cell *and maintain a*

*gradient of the portion of the liquid reagent back from the flow cell and fresh liquid reagent within the cache reservoir*; and a pump coupled to the flow cell and configured to draw the liquid reagent from the reagent reservoir into the cache reservoir and into the flow cell, and configured to return the at least a portion of the liquid reagent back to the cache reservoir for re-use.

14. The system of claim 13, comprising a valve coupled between the cache reservoir and the flow cell to direct the liquid reagent to the flow cell and back to the cache reservoir.

15. The system of claim 14, wherein the valve is configured to direct a portion of the liquid reagent from the flow cell to waste.

16. The system of claim 13, wherein the cache reservoir comprises an enlarged section of a reagent transport channel in the manifold.

17. The system of claim 13, wherein the manifold comprises a plurality of cache reservoirs for different liquid reagents.

18. The system of claim 13, wherein the cache reservoir comprises a volume less than the channel of the flow cell.

19. The system of claim 13, wherein the cache reservoir comprises a volume greater than the channel of the flow cell.

20. The system of claim 13, wherein the cache reservoir comprises a volume greater than a combined volume of more than one channel of the flow cell.

*21. The method of claim 1, wherein the transported at least 30% of the liquid reagent is downstream of at least part of the fresh reagent in the cache reservoir.*

* * * * *